United States Patent [19]

Malick et al.

[11] Patent Number: 5,580,735
[45] Date of Patent: Dec. 3, 1996

[54] STABILIZED MICROSPHERES AND METHODS OF PREPARATION

[75] Inventors: Adrien Malick, Granite; Hans H. Feindt, Parkton; Gerald D. Hahn, Severn, all of Md.

[73] Assignee: Becton, Dickinson and Company, Franklin Lakes, N.J.

[21] Appl. No.: 343,305

[22] Filed: Nov. 22, 1994

Related U.S. Application Data

[62] Division of Ser. No. 1,907, Jan. 4, 1993, Pat. No. 5,393,527.

[51] Int. Cl.$^6$ .............. G01N 33/531; C12Q 1/00; A61K 37/06

[52] U.S. Cl. ............... 435/6; 435/7.1; 435/7.5; 436/518; 436/524; 436/527; 436/528; 436/534; 436/829; 428/402.2; 427/2.11; 427/2.14; 427/2.23

[58] Field of Search .............. 435/6, 7.1, 7.5; 436/518, 524, 527, 528, 534, 829; 428/402.2; 427/2.11, 2.14, 2.23

[56] References Cited

U.S. PATENT DOCUMENTS

| | | | |
|---|---|---|---|
| 4,370,160 | 1/1983 | Ziemelis | 424/33 |
| 4,480,041 | 10/1984 | Myles et al. | 436/501 |
| 4,861,597 | 8/1989 | Kida et al. | 424/450 |
| 5,393,527 | 2/1995 | Malick et al. | 435/7.1 |

*Primary Examiner*—Christina Y. Chan
*Assistant Examiner*—Lora M. Green
*Attorney, Agent, or Firm*—Donna R. Fugit

[57] ABSTRACT

Stabilized microspherical particles having hydrophobic liquid cores prepared as oil-in-water microemulsions. The particles are stabilized by a surface layer comprising an amphiphilic compound and may be functionalized to allow covalent coupling of a ligand to the surface of the particle. When used as tracers in assays, a water insoluble dye may be incorporated in the core liquid of the microparticles.

5 Claims, No Drawings

STABILIZED MICROSPHERES AND METHODS OF PREPARATION

This is a division of application Ser. No. 08/001,907, filed Jan. 4, 1993, now U.S. Pat. No. 5,393,527.

FIELD OF THE INVENTION

The present invention relates to oil-in-water emulsions, methods for making such emulsions and methods for using the microspherical particles in diagnostic assays.

BACKGROUND OF THE INVENTION

Emulsions are fluid systems comprising two immiscible liquid phases with one liquid dispersed as droplets in the other. The dispersed liquid is referred to as the dispersed phase and the liquid in which it is dispersed is referred to as the continuous phase. Microemulsions are emulsions in which the dispersed phase droplets are very small, typically about 0.01 µm to about 0.2 µm. The choice of liquids for the two phases and the surfactants used determine whether the microemulsion is oil-in-water (o/w), water-in-oil (w/o) or anhydrous. Microemulsions are generally more stable than emulsions with discontinuous phases comprising larger droplets because the interfacial tension between the oil and water phases is significantly lower. That is, in microemulsions there is a reduced tendency for the droplets of the dispersed phase to coalesce.

Emulsions are generally made by subjecting the component liquids, including an emulsifier, to high shear forces. The forces may be mechanical, such as vigorous stirring or forcing the mixture through a small orifice. Alternatively, ultrasonic emulsification may be used to effect cavitation in the liquids with high local shear. As microemulsions provide a means for maintaining, in stable aqueous solution, substances which are otherwise insoluble in an aqueous phase, they are of interest as potential drug delivery systems for lipophilic drugs. Surface modifications on the dispersed phase droplets have been found to be useful for altering the physicochemical and biochemical properties of the colloidal droplets, including the kinetics of blood clearance and tissue distribution. (K. Iwamoto et al. 1991. J. Pharmaceutical Sciences 80, 219.)

As used herein, the term "water" in reference to emulsions means a polar hydrophilic liquid and is not limited to water per se. Similarly, the term "oil" in reference to emulsions means any nonpolar hydrophobic liquid. The terms "microspherical emulsion", "microemulsion" and related terms refer to stable emulsions in which the droplets of the dispersed phase are very small. "Microparticle", "microsphere", "particle", "microspherical particle" and related terms refer to the droplets of the dispersed phase of the microemulsion, which may or may not be emulsified in an aqueous phase. "Functionalized" particles, microparticles, droplets or microspheres have at least one amphiphilic component in the surface layer which includes a reactive group suitable for covalently coupling the microparticle to a ligand.

A ligand specifically recognizes and binds to a receptor molecule. The ligand and its receptor are referred to as a specific binding pair. The specificity of binding of a ligand and receptor can be used in assays for detection of an analyte which is either a ligand or receptor. Ligand/receptor pairs include, as examples, antigens or haptens and antibodies, complementary nucleic acids, biotin and avidin/streptavidin, and carbohydrates and lectins.

Methods for production of the microspheres of the invention are similar to the ethanol injection methods previously known for the preparation of liposomes. However, such methods have not heretofore been adapted for the production of particles with hydrophobic liquid cores and amphiphilic monolayers on the surface. The ethanol injection method for production of single bilayer liposomes encapsulating an aqueous medium is described by S. Batzri and E. Korn (1973. Biochim. Biophys. Acta 298, 1015.) and in *Liposomes—A Practical Approach* (IRL Press, R.R.C. New, ed., pg. 63). U.S. Pat. No. 5,100,591 describes methods for production of liposomes which incorporate an amphoteric, water-insoluble substance such as amphotericin B into the membrane with the phospholipids.

The stabilized microparticles of the invention are useful in a wide variety of applications where a hydrophobic particle core is desirable. Liposomes have previously been used for many of these applications, with various problems and disadvantages. In the present invention, the liquid hydrophobic core allows efficient incorporation of water-insoluble compounds for use in cosmetics (e.g., dyes and fragrances), foods (e.g., oils and flavors) and agriculture (e.g., insecticides and herbicides). Water-insoluble drugs may also be included in the core of the microparticles to improve drug delivery and stability in therapeutic applications. Such drug-containing microspheres are capable of incorporating more of the drug than the "pharmacosomes" of the prior art, which can only encapsulate the water-insoluble drug in the relatively small hydrophobic regions within the membrane bilayer rather than in the relatively large aqueous core. See Perrett, et al. 1991. J. Pharm. Pharmacol. 43, 154; Hamann, et al. 1989. 5th Internat. Conf. Pharm. Tech. 1, 99; Hamann, et al. 1987. Acta Pharm. Technol. 33, 67 for discussions regarding incorporation of drugs into liposomes. Further, amphiphilic drugs such as amphotericin B or insecticidal/herbicidal fatty acids may be incorporated as amphiphiles in the surface monolayer of the inventive microspheres for therapeutic and agricultural applications.

As the surface charge of the present stabilized microspheres can be increased by adjusting the types and amounts of amphiphilic drugs or amphiphilic lipids in the surface monolayer, they can be made to move with an electric potential while carrying pharmaceutical agents. They may therefore also be useful for delivery of drugs by iontophoresis.

SUMMARY OF THE INVENTION

Oil-in-water emulsions containing stabilized microspherical particles as the dispersed phase are provided. The microparticles comprise a liquid hydrophobic core with a surface coating of an amphiphilic compound. The microparticles or droplets of the dispersed phase may optionally be functionalized by inclusion of a reactive group on the surface for coupling to antibody, antigen, hapten or oligonucleotide ligands. Ligand-derivatized microparticles are useful as reagents in diagnostic assays involving binding of a ligand to its receptor and can replace other types of particulate reagents typically used in diagnostic assays, e.g., latex particles, metal sol particles, magnetic beads, colloidal particles or liposomes. If a water-insoluble dye is included in the core liquid, the microemulsions may also be used as tracers in the diagnostic assays to provide a reporter or detector function. The microspherical particles of the invention have the advantage of incorporating a higher concentration of dye than is possible using liposomes, as liposomes encapsulate a large amount of aqueous medium in addition to the entrapped dye. They are also more intensely colored than colored latex particles, thus improving assay sensitivity.

The microspherical particles of the oil-in-water emulsions have stabilized, non-drying, liquid cores and will readily rehydrate to approximately their original size upon reconstitution from a dried state. This is an improvement when compared to many other particle types such as latex, which do not resuspend easily after drying. In addition, the microparticles remain stable when stored at room temperature. When used as tracers, the microspheres will not leak the water-insoluble dye contained in the core into the surrounding aqueous medium. In contrast, liposomes containing water-soluble dyes tend to hydrate slowly and leak substantial amounts of dye upon reconstituion from a dried state. This difference in rehydration time is most likely due to the fact that the droplets need only be hydrated at their surfaces to function in an aqueous environment, whereas liposomes must be hydrated on their lipid bilayer surfaces as well as in their interior to function in an aqueous environment after lyophilization. Rapid rehydration with minimal loss of signal are highly desirable characteristics for tracer reagents, particularly when they are used in immunocapillary or immunochromatographic diagnostic tests.

DETAILED DESCRIPTION OF THE INVENTION

The stabilized microspherical particles of the invention are prepared as oil-in-water (o/w) microemulsions using water-insoluble compounds and mixtures of amphiphiles. The amphiphiles coat the dispersed droplets of the water-insoluble compound and stabilize them in the aqueous phase. Dyes soluble in the water-insoluble compound may optionally be included. In general, the microemulsions may be prepared by any of the methods known in the art, but certain modifications preferred. Because the amphiphiles are not soluble in the water-insoluble compound, a cosolvent is preferably initially included during the preparation of the emulsions. The cosolvent is then removed at a later stage of the preparation process.

The water-insoluble compounds which form the cores of the microspherical particles are liquid at room temperature and preferably have a high capacity to dissolve water-insoluble dyes if the microemulsions are to be used as tracers. Preferably, they withstand vaporization under conditions used for lyophilizing aqueous solutions and have a density equal to or slightly higher than the density of the aqueous environment in which they will be emulsified, i.e., usually about 1.0 or slightly higher. Water-insoluble compounds having these properties, when stabilized in a microemulsion, behave like solid particles when the microemulsion is lyophilized. The preferred water-insoluble compound for use in preparing the inventive microemulsions is polydimethyldiphenyl siloxane, such as GE Silicone SF 1154 available from General Electric Co., Waterford, N.Y. This silicone fluid has a density of 1.05, low viscosity and is non-volatile. Other silicones may also be used in the invention, for example GE SF 1265, or Huls America (Piscataway, N.J.) fluorosilicones PS 181 and PS 182. When fluorosilicones are used, a 1:1 mixture of DMF (dimethylformamide) and ethanol is required to bring the other components into solution.

The continuous phase of the microemulsions may be any aqueous compound suitable for the desired application. Examples of aqueous continuous phase compounds include water and various buffers as are known in the art.

The amphiphiles used to prepare the microemulsions stabilize the microparticles to the aqueous environment by preventing coalescence of the oil droplets, forming a layer on the surface of the dispersed oil droplet. This layer is believed to be a monolayer, in contrast to the bilayer membranes formed in liposomes. This structure is supported by experimental analysis showing that the ratio of maleimide on the surface of the microparticles to the total amount of maleimide in the particle is 1:1 (see the Examples). In contrast, liposomes give a ratio of 2:1 or higher depending on the size of the liposome and the number of bilayers it contains. Preferably, a mixture of amphiphiles is used. Suitable amphiphiles include the lipids typically used in the preparation of liposomes. Preferred amphiphiles are phospholipids such as phosphatidyl choline, phosphatidyl glycerol and phosphatidyl ethanolamine. Most preferred are the distearoyl phospholipids, e.g., distearoyl phosphatidyl choline (DSPC), distearoyl phosphatidyl glycerol (DSPG) and distearoyl phosphatidyl ethanolamine (DSPE). DSPE may be derivatized to include a maleimidyl caproate moiety (DSPE-MC) to functionalize the microparticle for coupling to a ligand. The charge of the microparticles may be adjusted for a particular pharmaceutical or iontophoresis application by increasing or decreasing the amount of DSPG or DSPE, or by treating the maleimide with MESA.

When the microparticles are to be functionalized, it is preferred that the amphiphilic component be a mixture of amphiphiles which includes at least one amphiphile which can be covalently linked to the selected ligand. The coupling amphiphile may be a derivatized phospholipid which carries a functional group suitable for covalent coupling of the ligand directly to the surface of the microparticle, e.g., a maleimidyl derivative of the phospholipid or thiocholesterol. Covalent methods are suitable for coupling antigen, antibody, happen and oligonucleotide ligands to the microparticle, the oligonucleotides preferably being linked through thio groups to a maleimide function on the phospholipid. Maleimide functionalized phospholipids may also be coupled to avidin, streptavidin or biotin which are then noncovalently bound to a biotin or avidin/streptavidin-derivatized ligand, resulting in indirect coupling of the ligand to the microparticle. H. C. Loughrey, et al. 1990. J. Immunol. Mtds. 132, 25. Biotinylated protein or oligonucleotide ligands may also be indirectly coupled to the surface of the microparticle via an anti-biotin antibody covalently coupled to the surface phospholipids.

Alternatively, an amphiphilic ligand may be included in the mixture of stabilizing amphiphiles which comprises the coating on the surface of the droplet. For example, cardiolipin, a four-chain phospholipid, is a suitable amphiphile for preparation of the microemulsions and is also useful as an antigen ligand for syphilis serology testing. Microparticles which include cardiolipin on their surfaces can be used in agglutination immunoassays for detection of anti-syphilis antibodies.

Cholesterol may be included with the amphiphiles but is generally not required as it is for liposomes because the amphiphiles form a monolayer on the microdroplet rather than a collection of bilayers as in liposomes. As the function of cholesterol in liposome membranes is to intercalate in and stabilize the liposome bilayers, it is optional in the present invention. Preferably, cholesterol is not included when the microparticles are used as tracers, as its presence may increase background staining and baseline levels of agglutination in certain solid phase immunoassays. It has also been found that increased amounts of DSPG increase the surface charge of the particles and prevent aggregation after antibody coupling, thereby reducing background and false positives when the microparticles contain a dye. Alternatively, treatment of the particles with MESA (2-mercaptoethanesulfonic acid) after coupling to the ligand also reduces background and false positives.

Water-insoluble dyes are optionally incorporated into the droplets of the o/w microemulsion to prepare tracer compositions for detecting analytes in diagnostic assays. Detectable tracers and tracers comprising dyes are well known in the art of specific binding assays, i.e., assays which involve binding of a ligand and its specific binding pair member. The water-insoluble compounds of the particle core are capable of dissolving the water-insoluble dyes at high concentration, thereby improving the sensitivity of the diagnostic assay. Suitable water-insoluble dyes are those known in the art for incorporation into tracers, e.g., encapsulation into liposomes or incorporated into latex particles. Different dyes may be incorporated into separate microparticle preparations which may then be mixed for use in assays for multiple analytes or where multisignal readouts are desired. A preferred dye for use in the invention is Sudan Black B.

When Sudan Black B (SBB) is incorporated into the microspherical particles, it is preferred that the dye first be purified. Purification and isolation of the major components of SBB are described by U. Pfuller, et al. 1977. Histochemistry 54, 237 and U. Pfuller, et al. 1977. Verb. Anat. Ges. 71, S 1439. Using preparative thin layer chromatography with chloroform as the mobile phase, the major fast moving (i.e., more hydrophobic) component can be isolated. This component is herein referred to as "Fast SBB." Fast SBB may also be isolated by chromatography on a silica column using dichloromethane:hexane 80:20 as the solvent or from TLC plates run in dichloromethane. Dichloromethane in general provides better separation of Fast SBB from Slow SBB than does chloroform. Sudan Black B commercially available from Eastman Kodak, Rochester, N.Y. is supplied as 98% pure, but Fast SBB comprises about 17% of the total weight (assuming 100% yield on purification). The use of Fast SBB provides for a more stable particle, incorporation of higher amounts of dye, and a more stable maleimide function than is possible using unpurified SBB. Purified Fast SBB will not partition into the aqueous phase either during particle formation or during rehydration of lyophilized particles and is therefore preferred for stability and intensity of the signal.

The purity of the Fast SBB preparation may be approximated after solubilization in ethanol by the absorbance ratio at 700 and 600 nm (extinction coefficient 24000):

|  | A700/A600 |
| --- | --- |
| Impure SBB | .23 |
| Slow SBB | .27 |
| Fast SBB | .08 |

In one embodiment, silicone microemulsions are made by dropwise addition of an ethanol solution of lipids, silicone and dye (optional) into the aqueous phase while mixing on a vortex mixer. This method results in a gradual increase in ethanol concentration from 0% to a finite level, usually less than about 50%. The ratio of ethanol to aqueous is apparently not critical within this range. Particles are preferably produced by mixing the ethanol solution with the aqueous phase to achieve a final concentration of ethanol of about 20–40%. Most preferably, the ethanol solution and the aqueous are mixed in a ratio of about 1:2, resulting in a final concentration of ethanol of about 30%. However, the ethanol concentration may be as high as about 50% if it is dried (e.g., using a 4A molecular sieve to remove IPA, benzene, water, etc.) and the lipid concentration is reduced. After formation of the microparticles, the ethanol is preferably removed, e.g., by ultrafiltration, column chromatography or dialysis. Removal of the ethanol is not essential for coupling the microparticles to a ligand, but it is preferred. If the particles are to be coupled to a ligand, they are preferably concentrated prior to coupling. This method is rapid and simple for small-scale production of microspheres, but is not amenable to large scale production.

A large-scale method for production of the microspheres uses pumps or syringes to bring the ethanol solution into contact with the aqueous phase, preferably with fluid streams coming together in a "Y" connection. This method is advantageous in that it can be automated. For example, pumps running at different speeds or a Zymark Corp. MASTER LABORATORY STATION with syringes of appropriate size controlled by stepper motors to deliver the components at a selected ratio provide a system that is automated, scalable and allows control of the ratio of ethanol to aqueous. This ensures consistent particle formation and particle size distribution. Such an automated system also allows for formation of the particles at a fixed ratio of ethanol solution to aqueous, which results in a fixed concentration of particles. Larger volumes of microparticles may be produced by running the pumps/syringes for longer time periods, increasing the sizes of the syringes, etc. No deterioration was observed when 10 and 25 ml syringes were used in place of 3 ml syringes. The syringe system is preferred because it may provide the additional benefit of increased shear force and mixing generated by the expulsion of the two fluid streams through the narrow syringe opening.

In both preparation methods, particles of defined size distribution less than 1 µm and typically less than 250 nm are formed without extrusion or sonication, as would be required for formation of liposomes of defined size. The ratio of lipids to silicone, the concentration of lipids and silicone in the ethanol and the ratio of organic volume (ethanol solution) to aqueous volume determine the particle size of the microemulsion. These ratios are adjusted to obtain the desired particle size during the formation of the microemulsion as, in contrast to liposomes, the microparticles cannot be resized after they have been made. Most preferably, the microemulsions have a particle size under 200 nm.

The organic cosolvent is a water miscible organic solvent which performs the function of solubilizing all of the components. Examples include short chain alcohols such as ethanol and dimethylformamide (DMF). Individually, the components are either insoluble in each other or insoluble in the organic cosolvent. For example, 1) lipids are not soluble in silicone and 2) DSPG and DSPE are not soluble in ethanol. However, as a combined system these components are soluble. The water-insoluble dye, if present, is soluble in silicone or lipids. It has also been found that the silicone allows incorporation of as much as ten times the amount of dye which can be incorporated without silicone (mM dye/ µM Pi without silicone=0.3, with silicone=3.0).

Preferably, when functionalized microparticles are to be coupled to a ligand they are typically first concentrated to about 100 nM maleimide per ml to increase the efficiency of coupling. The particles may be concentrated by dialysis, lyophilization and reconstitution or other suitable means known in the art. If desired, microparticles may be coupled to the ligand using appropriate protocols as described above, including forming a covalent linkage to a maleimide function on an amphiphile in the particle coating. When a protein is to be coupled, thiols are reduced prior to coupling. This protein may be the ligand itself (direct coupling) or it may be avidin, biotin or antibody for use in noncovalent coupling of the ligand to the microparticle.

In a preferred embodiment for producing a reagent for immunoassay, an antibody ligand is coupled to the particle at pH 8 and remaining free antibody is removed by column chromatography. A SEPHAROSE FAST FLOW column (Pharmacia LKB Biotechnology, Inc., Piscataway, N.J.) equilibrated in 30 mM MOPSO (3-[N-Morpholino]-2-hydroxy-propanesulfonic acid), 10 mM EDTA, 100 mM glucose, and 0.2% $NaN_3$, pH 6.8, is preferred. This buffer gives a good yield as a result of minimal sticking of particles to the column. Sucrose may be substituted for glucose in the buffer without adversely affecting subsequent lyophilization and reconstitution Of the particles. Additives such as glycerol/DMSO should be avoided due to unsatisfactory performance in assays after lyophilization and reconstitution. Dextran and beta hydroxy propyl cyclodextrin additives are optional and do not adversely affect performance of the particles after lyophilization.

The microparticles may be lyophilized for storage by freezing the microemulsion and lyophilizing it. The microemulsion may either be frozen slowly (e.g., at about–40° C. in the lyophilizer) or more rapidly in liquid nitrogen (about–150° C.). In one embodiment, the frozen microemulsions are lyophilized such that warming from about–40° C. to+25° C. occurs over a 4 to 12 hour period under vaccuum. The vials are then held at+25° C. until the lyophilization is complete. The lyophilized particles show improved performance in diagnostic assays when the vials are closed under vacuum in a low humidity environment after lyophilization. Conveniently, this can be done in the lyophilizer. This procedure reduces the background when the microemulsions are used as tracers in specific binding assays, thereby improving assay sensitivity and providing a cleaner system for evaluating and optimizing assay parameters.

The particles are preferably lyophilized in the presence of at least 1% of a stabilizing protein to improve stability of the functionalized microspherical particles during storage or treatment at elevated temperatures. Preferably the stabilizing protein is at least 1% BSA, more preferably 5% BSA (Pentex Fraction V BSA, Miles Laboratories, Kankakee, Ill.), but other proteins known in the art for this purpose are also suitable, e.g., casein. Particle concentration and the ratio of particles to stabilizing protein affect the level of background seen in diagnostic tests using reconstituted microemulsions. It has been noted that too little or too much BSA (13% or more) increases the background in the malaria test described in Example 3. The ratio of stabilizing protein to particles (quantitated by the amount of $P_i$) is preferably greater than 28 mg protein/1 µM $P_i$ and less than 200 mg/1 µM $P_i$.

The lyophilized microparticles, stored in closed containers, may be rapidly reconstituted (i.e., resuspended) in any suitable aqueous medium, for example water or a buffer. Suitable buffers include, for example, MOPSO/glucose, MOPSO/glucose/BSA and borate buffers. The reconstituted particles are similar in size to particles which have not been lyophilized. An appropriate dilution of particles for a desired application can be obtained by adjusting the amount of aqueous medium added to reconstitute the particles. Samples in vials which have been closed under vacuum in a low humidity environment after lyophilization reconstitute especially quickly.

Microparticles which include ligands according to the invention are useful in a wide variety of assays known in the art which utilize specific binding between a ligand and its receptor for detection of an analyte. Such assays include immunoassays and nucleic acid hybridization assays which can be performed in several different formats, as is known in the art. Certain of these assays include a tracer which becomes associated with the complex formed by binding of the ligand to its receptorand thereby facilitates detection of the complex. Detection of the complex is an indication of the presence, absence or quantity of the analyte, depending on the assay format. Conventional tracers comprise a ligand (an antibody, antigen or oligonucleotide) coupled to a detectable label such as a dye, a fluorescent compound, a radioisotope or an enzyme which can be reacted with a substrate to produce a colored product. The tracers of the invention, in contrast, comprise functionalized microparticles having the ligand associated with the surface such that it is capable of binding to a receptor, and a dye included in the hydrophobic liquid core. While the tracer microspheres may be substituted for conventional tracers in essentially any of the known immunoassay or nucleic acid hybridization assay formats, solid phase immunoassays are preferred because separation of reagents is faster and simpler than in other assay formats. A preferred solid phase assay device is an immunocapillary or immunochromatographic assay device, as the intensity of the dye color, the reduced background and fewer false positives associated with the microspherical tracers provide particular advantages in these types of assays.

Immunocapillary or immunochromatographic immunoassay devices comprise a microporous absorbent material such as nitrocellulose, nylon, methyl acetate, methyl cellulose or glass fiber. Alternatively porous materials which are not substantially absorbant, such as certain ceramics, may be used in such devices employing a vaccuum to draw reagents and sample into the material. To perform an immunoassay using such a device, a portion of the microporous absorbent material is contacted with a fluid sample such that the sample is drawn up into the device by capillarity (wicking), thus bringing the sample into contact with a capture reagent immobilized on the microporous absorbent at a position removed from the point of contact with the sample. The immobilized capture reagent is generally an antibody or antigen which serves to capture an antigen or antibody analyte in the sample by binding to it. In a competitive assay format, the ligand and the analyte are generally the same molecule or analogues which bind the same receptor. For a competitive assay the tracer and the sample are wicked up into the microporous absorbent simultaneously and compete for binding to the capture reagent. In a sandwich assay format, the analyte is generally a receptor for the ligand. The analyte is captured first and the tracer is wicked up into the microporous absorbent into contact with the captured analyte, binding to it as an indication of the presence of the analyte.

In one embodiment of an immunocapillary assay device employing the functionalized microparticle tracers of the invention, anti-malaria antibodies are coupled to the microparticles for detection of malaria antigen (the analyte) in a sandwich assay. An exemplary assay device is an immunocapillary dipstick having an anti-malaria capture antibody immobilized above the base of the stick. The end of the dipstick below the line of capture antibody is brought into contact with the sample to be tested and the sample fluid is drawn by capillarity into coiltact with the capture antibody. After binding of any analyte which may be present in the sample to the capture antibody, a composition comprising the microparticle tracer is drawn into contact with the captured malaria antigen, if present. Development of a detectable, preferably visible, line of dye in the region of the capture antibody is an indication of the presence of malaria antigen in the sample.

In a second embodiment, the functionalized microspherical particles (with or without incorporated dye) may be used in serological agglutination assays similar to the VDRL test for syphilis. In these assays, an antigen associated with disease may be covalently coupled to the surface of the microparticles or included in the amphiphilic monolayer coating on the surface. Mixing the functionalized microparticles with the serum of a patient which contains antibodies to the disease associated antigen results in cross-linking of the microparticles by antibody and visible particle aggregation. Alternatively, antibody may be coupled to the microparticles and used to detect an antigen present in serum by agglutination of the microparticles.

The following experimental examples are presented to illustrate certain specific embodiments of the invention but are not to be construed as limiting the invention as defined by the appended claims.

EXAMPLE 1

Preparation of Silicone Microemulsions

A mixture of 47 mg of distearoyl phosphatidyl choline (DSPC, Avanti Polar Lipids, Pelham, Ala.), 10.3 mg. distearoyl phosphatidyl glycerol (DSPG, Avanti Polar Lipids), 1.87 mg distearoyl phosphatidyl ethanolamine-maleimidyl caproate (DSPE-MC), 59 mg Fast Sudan Black B (Aldrich Chemical Co., Milwaukee, Wis. or Eastman Kodak, Rochester, N.Y.), 236 µl polydiphenyldimethyl siloxane (GE Silicone SF 1154, General Electric Co., Waterford, N.Y.) and 8.87 ml 200 proof ethanol (dried with a 4A molecular sieve and filtered with a Millipore GV syringe filter—Quantum Chemical Corp., USI Division, Tuscola, Ill.) was heated at 55° C. for 1 hour. The ethanol solution (1 part) was then mixed with water (3 parts) using a Zymark Corp. master laboratory station with 10 and 25 ml syringes controlled by stepper motors. The fluid streams were mixed in a "Y" connection, resulting in instantaneous particle formation. After formation of the microemulsions, ethanol was removed by dialysis against 10 mM EDTA and the microemulsions were concentrated by dialysis against a dessicant. The size of the particles, as determined by analysis with a Coulter Corp. (Hialeah, Fla.) model N4 MD sub-micron particle analyzer, was about 187 nm by unimodal analysis. The phosphorous concentration was determined to be 3.4 µM $P_i$/ml, and the maleimide was determined to be 98.8 nM MC/ml.

EXAMPLE 2

Coupling of Microparticles to Antibody

The microparticles prepared in Example 1 were coupled to rabbit anti-recombinant HRP II antibody. These antibodies are directed against the histidine rich protein II antigen of Plasmodium falciparum, the etiological agent of malaria. Anti-HRP II antibody was dialyzed into phosphate buffered saline (PBS), pH 8, resulting in a concentration of 2.47 mg/ml as determined by absorbance at 280 nm with an extinction coefficient of 1.35. Six mg of antibody was derivatized with SPDP (3-(2-pyridyldithio propionic acid N-hydroxysuccinimide ester, Sigma Chemical Co., St. Louis, Mo.) for 30 min. using a solution of 1.5 mg SPDP in 1.5 ml methanol (60 µl). 1M sodium acetate, pH 4.5 (280 µl) was then added and followed by 86 µl of 1M dithiothreitol (DTT), resulting in a final DTT concentration of 33 mM. The solution was stirred at room temperature for an additional 30 min., then applied to a SEPHADEX G-25 column (Pharmacia LKB Biotechnology, Inc.) to remove free DTT and place the derivatized antibody into pH 8 coupling buffer (50 mM Tris Base, 50 mM sodium acetate, 50 mM sodium chloride and 1 mM EDTA).

The concentration of antibody was determined by absorbance at 280 nm. The antibody preparation was mixed with the microemulsion, which had been brought to pH 8 with Tris immediately before use, at a ratio of 1 mg antibody per 100 nM maleimide. The mixture was incubated for 2 hours. The functionalized particles were then separated from free antibody on a SEPHAROSE FAST FLOW column (Pharmacia LKB Biotechnology, Inc.) equilibrated in 30 mM MOPSO, 10 mM EDTA, 100 mM glucose, and 0.2% sodium azide, pH 6.8. Miles Pentex Fraction V BSA was added to give a final w/v concentration of 1%.

EXAMPLE 3

Immunoassay Using Tracer Microspheres

Immunocapillary assay devices for detecting malaria antigen were prepared as follows. A 2.8 cm×15 cm strip of 8 micron nitrocellulose (Schleicher and schuell, Keene, N. H.) was laminated onto plastic. A monoclonal capture antibody raised in response to an 18-mer peptide with an amino acid sequence derived from the tandem repeat sequence of HRP II was spotted onto the nitrocellulose using a 1 mg/ml solution of the antibody applied at a rate of 1 µg/cm². Two hybridomas which produce the anti-18mer antibody have been deposited with the American Type Culture Collection (Rockville, Md.) under Accession Numbers HB 11111 and HB 11112. The membrane strips were then incubated at 45° C. for 15 min. and blocked with a solution of 5 mM EDTA, 5% beta lactose, 0.2% $NaN_3$, 0.2% ZWITTERGENT 3-10 (Calbiochem, LaJolla, Calif.) and 1% BLOTTO (nonfat dry milk). The blocked strips were placed at 45° C. overnight. The prepared membranes were applied to a 7 cm×15 cm strip of laminated plastic and overlapped with a 4.7 cm×15 cm piece of glass fiber (Gelman Sciences, Ann Arbor, Mich.) to assist in drawing fluids into the nitrocellulose. The strips were cut into 7 mm wide test sticks and stored dessicated.

For the assay, the malaria test sticks were placed in a test tube with 40 µl of normal human serum (NHS) containing various dilutions of the 18-mer peptide as the analyte. The 18-mer is a unique synthetic peptide comprising the following amino acid sequence, SEQ ID NO: 1:

Cys—Gly—Ala—His—His—Ala—His—His—Ala—Ala—Asp—
Ala—His—His—Ala—Ala—Asp—Ala.

The microparticle tracer prepared in Examples 1 and 2 was diluted 1:3 with MOPSO buffer containing 1% BSA and 40 µl of the diluted tracer was added to the tube after the serum sample had been wicked up into the test stick. After allowing the tracer to be drawn into the test stick, 40 µl of a wash solution (pH 7.5 borate buffer with 0.2% ZWITTERGEN 3–10) was added and also allowed to wick up. The degree of color in the area of the capture antibody line was visually determined and assigned a subjective number based on the intensity. Endpoints for detection of the signal were typically at antigen dilutions of about $1\times10^{-7}$ indicating a highly sensitive assay.

The test results are summarized in the following Table. Preparation A (the microparticle tracer) is compared to a liposome tracer encapsulating sulforhodamine B (Lot 002).

| PARTICLE PREP. | NHS | DILUTION | | | |
|---|---|---|---|---|---|
| | | $10^{-4}$ | $10^{-5}$ | $10^{-6}$ | $10^{-7}$ |
| A | — | 4 | 3 | 2 | 1+ |
| Lot 002 | WK+1 | 4 | 3 | 2 | 1 |

These results demonstrate that the assay using the microparticle tracers detects a clinically relevant amount of malaria antigen and is comparable in performance to a liposome tracer encapsulating dye.

EXAMPLE 4

Lyophilization and Reconstitution of Microparticles

Microemulsions prepared as in Examples 1 and 2 were stored in MOPSO buffer with 1% Miles Pentex Fraction V BSA. Aliquots of 166 μl were placed in vials with 333 μl of MOPSO buffer/1% BSA. Stoppers were loosely placed on the vials. The vials were frozen in liquid nitrogen and placed on a frozen shelf in a lyophilizer (The Virtis Co., Inc., Gardiner, N.Y.). The lyophilization cycle was controlled such that the shelf warmed from −40° C. to +25° C. over a 12 hour period under vacuum. The condenser remained at −40° C. The vials were held at 25° C. until the run was complete, a minimum of approximately 18 hours. The vials were then stoppered in the lyophilizer, under vacuum and at low humidity, by filling a bladder under the tray with room air. The stoppered vials were stored for 11 days at 45° C.

To reconstitute the microemulsions, the stopper was removed and a volume of MOPSO buffer/1% BSA was added to correspond to the desired dilution of particles. For use in the immunoassay of Example 3, 500 μl of buffer was added to reconstitute the microemulsions. Rehydration occurred quickly, forming microemulsions containing 238 nm particles. Activity of the reconstituted microemulsion tracers was determined in an immunoassay as in Example 3. The results were as follows:

| | NHS | $1 \times 10^{-4}$ | $1 \times 10^{-5}$ | $1 \times 10^{-6}$ | $1 \times 10^{-7}$ |
|---|---|---|---|---|---|
| ACTIVITY | +/− | +4 | +2 | +1 | +/− |

EXAMPLE 5

Cardiolipin Microspheres

Phosphatidyl choline (10 mg, either DSPG, Avanti Polar Lipids or L-alpha mixed chains, Sigma Chemical Co.) was mixed with 1 mg DSPG, 40 μl SF 1154 silicone, 50 μl cardiolipin (Sigma Chemical Co., 5.2 mg/ml in ethanol) and 1.5 ml ethanol. DSPG is optional. The solution was heated at 55° C. for 1 hour, then added dropwise through a Gelman 4450 0.2 μm 13 mm filter to 4.5 ml water mixing on a vortex. The resulting microemulsions contained 174 nm particles. The microemulsions were dialyzed in SPECTRA/POR 2 dialysis bags (Spectrum Medical Industries, Inc., Los Angeles, Calif., 12–14000 MW cutoff) against 10 mM EDTA overnight to remove ethanol.

Commercially available VDRL antigen (Difco Laboratories, Detroit, Mich.) contains 0.03% cardiolipin, 0.21% lecithin and 0.9% cholesterol in ethanol. This ethanol solution was added to formaldehyde buffered saline, forming a colloidal suspension. The suspension was centrifuged and resuspended in 0.02M phosphate buffer, pH 6.9 containing 0.2% merthiolate, 40% choline chloride and 0.1M EDTA. This preparation was referred to as "USR reagent." Both the USR reagents and the microemulsion were used to test sera for reactivity against cardiolipin as an indicator of exposure to syphilis.

One drop of the microemulsion or USR reagent delivered through an 18 gauge needle onto a ringed glass slide containing 50 μl of saline, serum or serum diluted in saline. The slide was rotated at 180 RPM for 4 min., and agglutination was read microscopically at 100×magnification. The highest dilution showing visible agglutination was determined to be the titer. Representative data is shown in the following table:

| | Silicone Microemulsions | USR |
|---|---|---|
| Antiserum 110 | neg | neg |
| Antiserum 114 | neg | pos 1:2 |
| Antiserum 115 | pos 1:2 | pos 1:2 |
| Antiserum 119 | pos 1:8 | pos 1:8 |

These results show that, using antiserum of known reactivity, in most cases the cardiolipin microparticle preparations exhibit reactivity similar to the standard, commercially available syphilis serology test.

---

What is claimed is:

1. A method of making microspherical particles comprising:
   a) preparing a solvent solution comprising a water miscible organic solvent, a liquid silicone compound and an amphiphilic compound having a functional group for covalent coupling to a ligand;
   b) combining said solvent solution with an aqueous medium to form an oil-in-water microemulsion having as the dispersed phase microspherical particles comprising a core and a monolayer on the surface of the core, wherein the core comprises the liquid silicone compound and the monolayer on the surface of the core comprises the amphiphilic compound;
   c) covalently coupling the ligand to the functional group of the amphiphilic compound, and;
   d) isolating the microspherical particles covalently coupled to the ligand.

2. The method of claim 1 wherein said solvent solution further comprises a water-insoluble dye.

3. The method of claim 2 wherein said liquid silicone compound is selected from the group consisting of polydimethyldiphenyl siloxane and fluorosilicones and said amphiphilic compound is a phospholipid selected from the group consisting of phosphatidyl choline, phosphatidyl glycerol, phosphatidyl ethanolamine and distearoyl derivatives thereof.

4. The method of claim 3 wherein said ligand is selected from the group consisting of antibodies, antigens, haptens, biotin, avidin and oligonucleotides.

5. The method of claim 1 wherein said water miscible organic solvent is removed prior to covalently coupling the ligand to the amphiphilic compound.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

| | | | | | | | | | | | | | | |
|---|---|---|---|---|---|---|---|---|---|---|---|---|---|---|
| Cys | Gly | Ala | His | His | Ala | His | His | Ala | Ala | Asp | Ala | His | His | Ala Ala |
| 1 | | | | 5 | | | | | 10 | | | | | 15 |
| Asp | Ala | | | | | | | | | | | | | |